United States Patent [19]

Holling

[11] Patent Number: 4,569,095

[45] Date of Patent: Feb. 11, 1986

[54] SAFETY BELT SYSTEM FOR A PATIENT STRETCHER

[75] Inventor: Gerd Holling, Eulenweg, Fed. Rep. of Germany

[73] Assignee: Christian Miesen Fahrzeug-und Karosseriewerk GmbH, Bonn, Fed. Rep. of Germany

[21] Appl. No.: 609,265

[22] Filed: May 11, 1984

[30] Foreign Application Priority Data

May 11, 1983 [DE] Fed. Rep. of Germany ... 8314066[U]

[51] Int. Cl.[4] ........................ A61G 1/00; A47C 27/08; A61F 13/00

[52] U.S. Cl. .......................................... 5/82 R; 5/424; 128/134

[58] Field of Search ............... 5/82 R, 82 B, 89, 81 R, 5/81 B, 81 C; 128/134; 24/632; 244/151 R

[56] References Cited

U.S. PATENT DOCUMENTS

| | | | |
|---|---|---|---|
| 2,520,710 | 8/1950 | Brown | 128/134 |
| 3,046,982 | 7/1962 | Davis | 128/134 |
| 3,088,128 | 5/1963 | Waddington | 5/82 |
| 4,064,574 | 12/1977 | Schnitzler | 5/82 R |

FOREIGN PATENT DOCUMENTS

| | | | |
|---|---|---|---|
| 62312 | 5/1975 | Australia | 5/82 |
| 8125289 | 8/1981 | Fed. Rep. of Germany . | |
| WO81/00103 | 2/1982 | PCT Int'l Appl. | 5/82 B |
| 1256657 | 12/1971 | United Kingdom . | |
| 1506926 | 5/1975 | United Kingdom . | |

*Primary Examiner*—Kenneth J. Dorner
*Assistant Examiner*—Vinh Luong
*Attorney, Agent, or Firm*—Armstrong, Nikaido, Marmelstein & Kubovcik

[57] ABSTRACT

A safety belt system for a patient stretcher (1) comprises an upper belt loop (6) which surrounds the lying surface (1*d*) of the stretcher in the patient's shoulder region, also a lower belt loop (3) which surrounds the lying surface (1*d*) in the region of the patient's feet. Two shoulder belts (8*a*,8*b*) are each secured at one end to the upper belt loop (6) and at their other end are connected via a quick-action fastening (12, 13) to the lower belt loop (3). The belt loops (3, 6) consist at least partly of elastically stretchable material and hold around the lying surface (1*d*) of the stretcher because of their elasticity, so that the safety belt system can be used in all normal stretchers and independently of whether there is an overlay lying on the stretcher or not.

8 Claims, 3 Drawing Figures

SAFETY BELT SYSTEM FOR A PATIENT STRETCHER

The invention relates to a patient stretcher having frame and/or feet parts which are capable of being positively secured on a supporting apparatus or stretcher platform in ambulance vehicles or ambulance aircraft, and having a safety belt system holding fast the shoulders of a patient lying on the stretcher, with an upper belt loop surrounding the lying surface of the stretcher in the shoulder region of the patient, two shoulder belts being secured to the said loop, with a lower belt loop which is arranged at the foot region of the stretcher and which surrounds the lying surface of the stretcher, and with a quick-action safety belt fastening comprising two interlockable and separatable fastening parts, one of which is held on those ends of the shoulder belts which are remote from the upper belt loop and the other is connected to a belt piece secured to the lower belt loop.

A stretcher with a safety belt system of this kind is known from German Utility Model No. 81 25 289. The safety belt system in this case is intended, more particularly if the ambulance vehicle brakes sharply or there is a more particularly frontal collision, to prevent the patient, who is usually arranged on the stretcher with his or her head in the direction of travel, as considered in the longitudinal direction of the stretcher, from sliding off the stretcher. In the case of the belt system according to the aforesaid Utility Model, certain belt parts are fixed to the stretcher frame to achieve the securing of the belt system to the stretcher.

In contrast, the present invention has as its object to develop the belt system in a stretcher further in such a manner that it can be used in all normal stretchers and irrespective of whether an overlay is situated on the stretcher or not.

This object is achieved according to the invention in that the belt loops consist at least partly of elastically stretchable material, and surround the lying surface of the stretcher with a holding action because of their elasticity.

Therefore, contrary to the state of the art, the belt loops supporting the actual restraining belts are not made of substantially non-elastic material, nor are they fixed to frame parts of the stretcher. On the contrary, in the case of the present invention the belt loops are of stretchable construction, so that they adapt within certain limits to any width of stretcher, and in the case of a specific stretcher they can be used selectively with or without an overlay, and in every case hold fast, elastically, about the stretcher with or without an overlay thereon.

In an advantageous feature of the invention it is proposed that the belt piece secured to the lower belt loop is held longitudinally displaceably on the fastening part associated with said piece. As a result it is possible in a simple manner to adapt the length of the belt system and the tension thereof to the dimensions of the patient lying on the stretcher.

According to a further advantageous feature of the invention a tension belt is also provided which connects the upper belt loop to the lower belt loop, and which is advantageously guided on the top side of the lying surface of the stretcher facing towards the patient. In the event of upwardly directed loading of the belt system this tension belt in a simple manner prevents the upper belt loop from slipping away in an upward direction.

Preferably the lower belt loop extends around the frame parts below the feet parts fixed to the frame parts, so that as a result the lower belt loop is prevented from slipping upwards, in a simple manner.

According to a further feature of the invention the two shoulder belts are made as a one-piece belt to which one of the fastening parts, the upper, is displaceably secured, so that it is possible for the shoulder belt to adjust automatically to any side by displacement within the fastening part.

Further advantageous features of the invention are shown in the other subordinate claims in conjunction with the following description, wherein a preferred example of embodiment of the invention is discussed in more detail with reference to the drawings.

Figure 1:
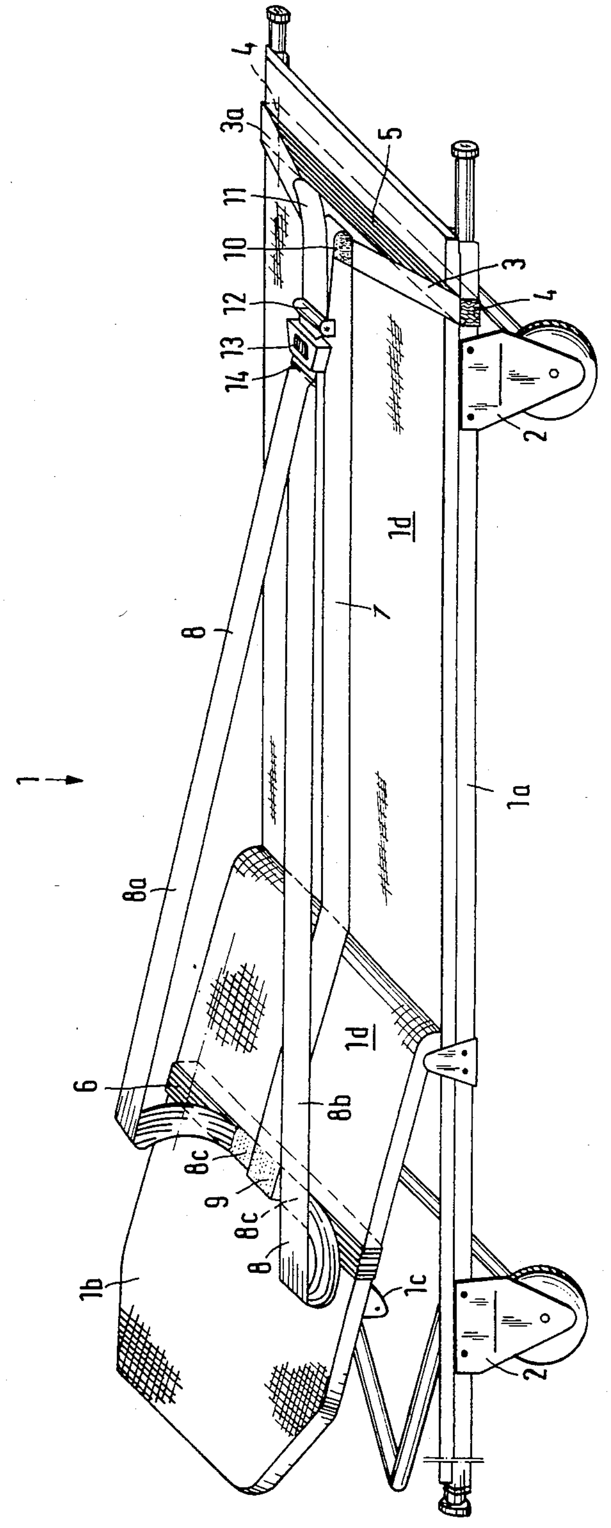
FIG. 1 shows in perspective view a stretcher with the safety belt system.
Figure 2:
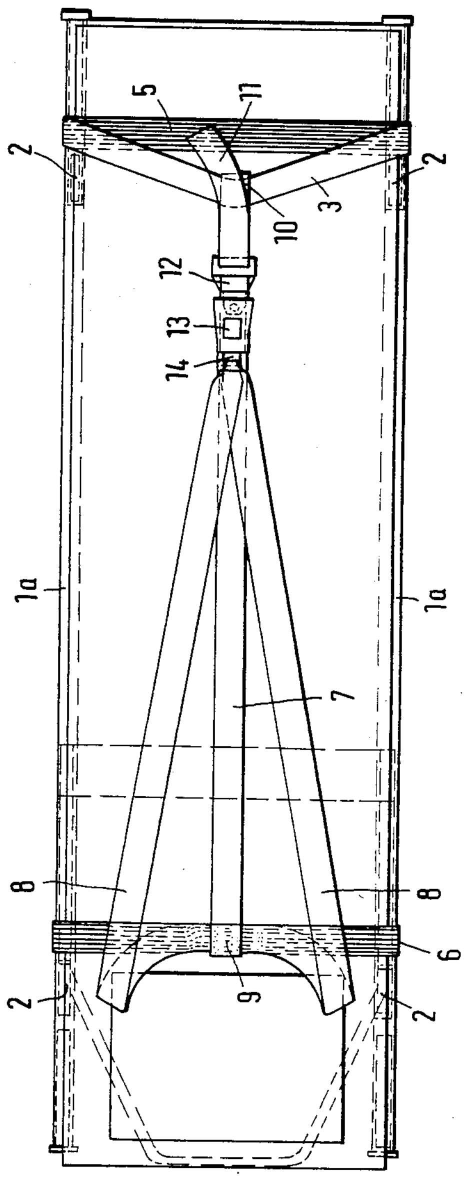
FIG. 2 shows a plan view from above of the stretcher according to FIG. 1.
Figure 3:
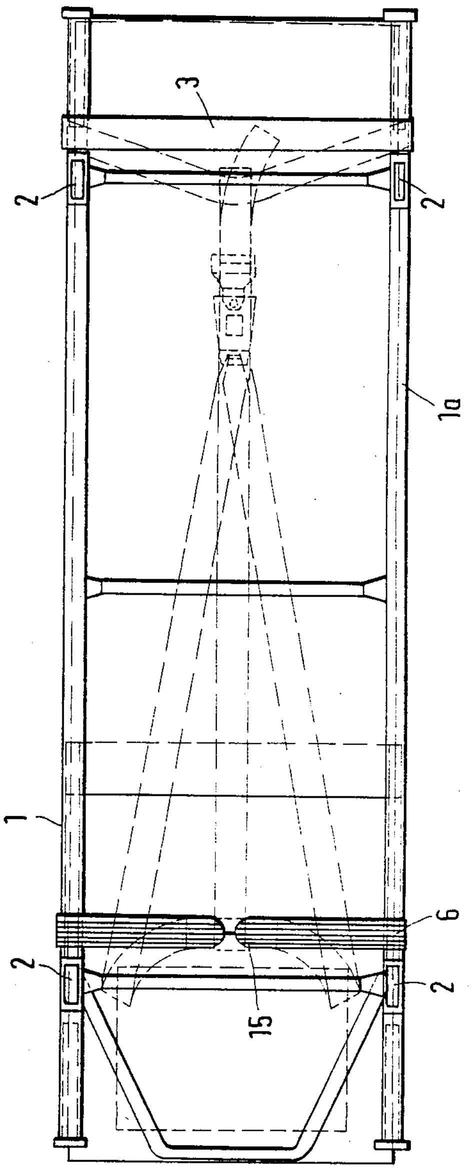
FIG. 3 shows a plan view from below of the stretcher according to FIG. 1.

The stretcher 1 comprises a frame 1*a* on which four stretcher feet 2 (with their wheels mounted, if appropriate) are fixed. Arranged at the foot end of the stretcher, below the feet 2 as seen in the longitudinal direction of the stretcher, is a lower belt loop 3 which with a holding action surrounds the stretcher possibly including an overlay arranged on the stretcher. The lower belt loop 3 comprises a belt portion 3*a* which is situated above and which consists of substantially non-elastic belt material, also a lower belt portion 5 which consists of elastic belt material. At 4 the upper belt portion 3*a* and the lower belt portion 5 are sewn to one another. Owing to the elastic belt portion 5*a* the lower belt loop 3 adapts itself in a simple manner to the particular stretcher in question, with or without an overlay, and at the same time it is ensured that the lower belt loop 3 is held securely on the foot end of the stretcher, below the stretcher feet 2.

At the head part 1*b* of the stretcher, approximately at the height of the patient's shoulders, a further holding loop 6 is situated, which holds elastically around the head part 1*b* and possibly an overlay which may be situated thereon but is not shown here. If appropriate the upper belt loop 6 may be arranged below, looking in the longitudinal direction of the stretcher, a frame projection 1*c* which prevents the upper loop from slipping upwards. In the case of the present example of embodiment the upper belt loop 6 consists preferably entirely of elastically stretchable belting.

A shoulder belt 8 comprises the two shoulder belts 8*a* and 8*b* whose upper regions are passed around the shoulders of the patient lying on the stretcher and whose two ends 8*c* are sewn securely to the upper belt loop 6. The shoulder belt 8 is taken displaceably through a loop 14 of the fastening part 13 of a quick-action safety belt fastening, the other part of said fastening being designated as 12. A belt piece 11 is held on the other fastening part 12 in a manner known per se such that it can be secured to give it various lengths. The belt piece 11 represents a prolongation of a tension belt 7 one end of which is sewn at 9 to the upper belt loop 6 and which in its lower region at 10 is securely sewn to the lower belt loop 3, and the then following piece of the tension belt 7 forms the belt piece 11 which is used for adjusting the tension of the belt system. The tension belt extends approximately centrally along the longitudinal direction of the reclining or lying surface 1*d* of the stretcher. When there is a patient on the stretcher the tension belt 7 extends below the patient, whilst the shoulder belt 8 is taken above the patient.

To allow the belt system to be put easily on to the stretcher, the upper belt loop 6 is made to be divided below the stretcher and can be fastened by means of a suitable fastening 14.

I claim:

1. A stretcher having a frame, a patient support surface and a safety belt system for holding a patient onto the stretcher, said safety belt system comprising:

(a) an upper belt loop surrounding the support surface of the stretcher in the region of the patient's shoulders, said upper belt loop belt having at least a portion of its circumference formed from an elastic material;

(b) a lower belt loop surrounding the foot region of the stretcher, said lower belt loop having at least a portion of the circumference formed from an elastic material;

(c) a pair of shoulder belts secured to said upper belt loop;

(d) a tension belt attached to said upper belt loop between said shoulder belts, traversing the support surface of the stretcher and being secured to said lower belt loop; and (e) a quick-release buckle having a tongue portion connected to said lower belt loop and a clasp portion to which the ends of said shoulder belts are secured.

2. The stretcher according to claim 1, wherein said tongue portion of said quick-release buckle is adjustably connected to said lower belt loops by a belt secured to said lower belt loop.

3. The stretcher according to claim 2, wherein said belt adjustably connected to said tongue portion is an extension of said tension belt.

4. A stretcher according to claim 1 wherein the tension belt is permanently secured to the upper belt loop.

5. A stretcher according to claim 1, wherein the upper belt loop is made completely of elastic material, and at the underside of said upper belt loop includes a fastening allowing the opening of the belt loop.

6. A stretcher according to claim 1, wherein the lower belt loop includes an insert portion made of elastic belting.

7. A stretcher according to claim 1, wherein the lower belt loop surrounds the frame below the feet portions which are fixed to the frame.

8. A stretcher according to claim 1 wherein the pair of shoulder belts are of one-piece and to which the clasp portion of the quick release buckle is adjustably secured.

* * * * *